(12) United States Patent
Del Soldato et al.

(10) Patent No.: US 6,512,137 B1
(45) Date of Patent: Jan. 28, 2003

(54) SYNTHESIS METHOD OF NITROXYMETHYLPHENYL ESTERS OF ASPIRIN DERIVATIVES

(75) Inventors: Piero Del Soldato, Milan (IT); Michele Garufi, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/868,932

(22) PCT Filed: Jan. 18, 2000

(86) PCT No.: PCT/EP00/00353
§ 371 (c)(1),
(2), (4) Date: Jul. 17, 2001

(87) PCT Pub. No.: WO00/44705
PCT Pub. Date: Aug. 3, 2000

(30) Foreign Application Priority Data

Jan. 26, 1999 (IT) .......................................... MI99A0134

(51) Int. Cl.[7] ................................................ C07C 69/00
(52) U.S. Cl. ...................................................... 560/143
(58) Field of Search ........................................ 560/143

(56) References Cited

U.S. PATENT DOCUMENTS 5,589,490 A * 12/1996 Sala et al. .................. 514/330
6,278,014 B1 * 8/2001 Handal-Vega et al. ...... 560/143

* cited by examiner

*Primary Examiner*—Deborah C. Lambkin
(74) *Attorney, Agent, or Firm*—Arent Fox Kintner; Plotkin & Kahn PLLC

(57) ABSTRACT

The invention describes a method for the synthesis of nitroxymethylphenyl esters of aspirin derivatives.

5 Claims, No Drawings

SYNTHESIS METHOD OF NITROXYMETHYLPHENYL ESTERS OF ASPIRIN DERIVATIVES

This Application is a 371 of PCT/EP00/00353 Jan. 18, 2000.

The present invention relates to an improved synthesis for obtaining (nitroxymethyl)phenyl esters of aspirin derivatives.

These esters have interesting pharmacological and therapeutical properties; specifically they show an improved systemic and local tolerability, at the level of the gastric mucosa (WO 95/030641) and they are more effective as antithrombotic medicines (WO 97/16405).

It is known in the prior art that the (nitroxymethyl)phenyl esters of the aspirin derivatives are prepared by reacting (nitroxymethyl)phenol with the aspirin derivative in the acid form (WO 97/16405).

In particular the preparation of (nitroxymethyl)phenol is carried out starting from (hydroxymethyl)phenol through the following steps:

reaction of phenol with HBr in an organic solvent to obtain (bromomethyl)phenol;

reaction of (bromomethyl)phenol in an organic solvent with $AgNO_3$ to form (nitroxymethyl)phenol.

The synthesis of the (nitroxymethyl)phenol intermediate has the following drawbacks. The (bromomethyl)phenol is a chemically unstable and irritant compound. The nitroxy derivative obtained from (bromomethyl-)phenol is still an unstable compound, which must be purified before reaction with the acid chloride. The (nitroxymethyl)phenol may further decompose in a not controllable way; consequently in order to obtain, on an industrial scale, the compound with the required purity for the final esterification step, the purification processes normally used in laboratory organic syntheses cannot be employed.

In conclusion the use of (nitroxymethyl)phenol in the synthesis of (nitroxymethyl)phenyl esters of aspirin derivatives is not industrially practicable.

It has been surprisingly and unexpectedly found by the Applicant that it is possible to synthetize (nitroxymethyl) phenyl esters of aspirin derivatives, and specifically (nitroxymethyl)phenyl esters of the N-acetylsalicylic acid, by synthetic reactions by which it can be avoided the use of the above mentioned phenol derivatives, and thus the purification steps of the intermediate compounds, obtaining the final products in good yields. Thus the new process is more advantageous than those of the prior art.

It is therefore an object of the present invention a new process for obtaining (nitroxymethyl)phenyl esters of aspirin derivatives of formula R—COOH wherein R is selected from one of the radicals having the following formula:

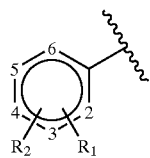

Ia)

-continued

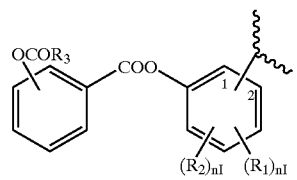

Ib)

wherein:

$R_1$ is the $OCOR_3$ group; wherein $R_3$ is methyl, ethyl or alkyl $C_3$–$C_5$, linear or branched, or the residue of a saturated heterocyclic ring having 5 or 6 atoms, containing heteroatoms independently selected between O and N; $R_2$ is hydrogen, halogen, $C_1$–$C_4$ alkyl, linear or branched when possible, $C_1$–$C_4$ alkoxyl, linear or branched when possible; $C_1$–$C_4$ perfluoroalkyl, linear or branched when possible, for example trifluoromethyl; nitro, mono- or di-($C_{1-4}$) alkylamino; $R_1$ and $R_2$ taken together are the dioxymethylene group, with the proviso in the formula Ib) that $R_1$ cannot be $OCOR_3$ in position 2 when $R_3$ is methyl;

nI is an integer and can have the values 0 or 1;

preferably in Ia) $R_1$ is acetoxy, preferably in ortho position with respect to the —CO— group, $R_2$ is hydrogen;

preferably in Ib) $R_3=CH_3$, nI=0;

preferably R—COOH is the acetylsalicylic acid; said process comprising the following steps, generally carried out in the presence of a solvent inert under the reaction conditions:

(1) reaction between the acid halide R—C(O)—X— wherein:

$X_I$ is an halogen selected between Cl and Br, R is a radical as above defined, in the presence of a base, with an isomer of the hydroxybenzaldehyde, i.e., wherein the hydroxyl group can be at ortho, meta or para position, with formation of a (carbonyl)phenyl ester (I):

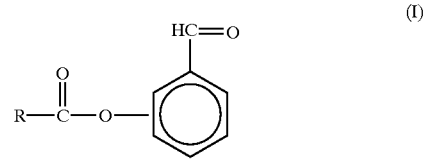

(I)

(2) selective reduction of the aldehydic group of compound (I) with formation of an (hydroxymethyl)phenyl ester (II):

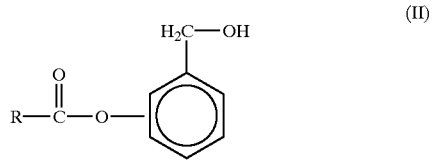

(II)

(3) reaction between the (hydroxymethyl) phenyl ester of formula (II) with:

a) $SOX_2$, X being an halogen selected between Cl and Br, with formation of an (halogenomethyl)phenyl ester of formula (III), wherein X=halogen, or b) tosyl chloride or mesyl chloride with formation of a (tosyloxymethyl)- or (mesyloxymethyl)-phenylester, X being=O-tosyl or O-mesyl in formula (III):

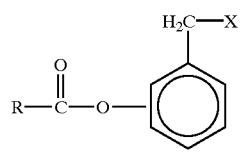

(III)

(4) reaction between the compound of formula (III) with an inorganic nitrate salt, the metal cation of which belongs to the group IB or IIB, with formation of the corresponding (nitroxymethyl) phenyl ester

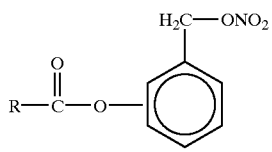

(IV)

The formation of the (carbonyl)phenyl ester of step (1) can alternatively be achieved by other reactions. For example by reaction of the aspirin derivative of general formula R—COOH with a dehydrating agent, such as for example N, N'-dicyclohexylcarbodiimide, in the presence of an aminopyridine derivative N, N disubstituted with alkyl radicals $C_1$–$C_4$ (step (1')), or with a $C_1$–$C_4$ alkylchloroformate in the presence of a base, soluble or insoluble in the reaction medium, as defined hereinafter (step (1")), or with N, N' carbonyldiimidazol (step (1''')).

The process object of the present invention allows to obtain products at the required purity degree. Thus it is not necessary to purify the product compounds obtainable after each step. The overall yields are good (50–70%).

In step (1), the aspirin derivative acyl chloride or bromide, prepared from the corresponding compound in the acid form by using known reactants (ex. thionyl chloride, thionyl bromide, oxalyl chloride, oxalyl bromide, $PCl_3$, $PBr_3$), is let react in inert solvents (for example halogenated hydrocarbons such as dichloromethane, trichloromethane; ethers, such as ethyl ether, propyl ether, isopropyl ether, dioxane; esters such as ethyl acetate, propyl acetate, butyl acetate), in the presence of an organic or inorganic base, with an hydroxybenzaldehyde isomer as above defined. Said base can be soluble in the reaction solvent, as in the case of tertiary aliphatic amines of formula $N(R_N)_3$, wherein $R_N$ is an alkyl group $C_1$–$C_4$, such as for example tributylamine, triethylamine, diethylmethylamine, trimethylamine; or said base can either be insoluble in the solvent, such as for example in the case of alkaline inorganic salts, for example, potassium carbonate, sodium carbonate, or alkaline metal bases such as NaOH and KOH.

When step 1) is substituted with step (1') as above defined, the aminopyridine derivative N, N disubstituted with alkyl radicals $C_1$–$C_4$, used in combination with the dehydrating agent, is preferably selected for example from dimethylamino pyridine and dibutylamino pyridine; when instead step (1") is used, the compound $C_1$–$C_4$ alkylchloroformate is preferably selected between ethylchloroformate and isobutylchloroformate.

The reaction (2) of selective reduction of the aldehydic group to alcohol can be carried out by hydrogenation with gaseous hydrogen using conventional catalyts supported on carbon, such as for example, palladium, in a solution of the compound of formula (I) in an inert solvent. The reaction temperature is in the range 0–40° C., the gas pressure can range from 1 to 3 atm.

In alternative to the hydrogenation with gaseous hydrogen, reduction of compound (II) can be effected also with other reducing agents, for example inorganic mixed hydrides, such as for example $NaBH_4$, under the conditions well known to the skilled in the field.

Step (3) is carried out in an inert organic solvent at a temperature in the range 0°–40° C.

The alternative reaction between the alcohol and the tosyl chloride or mesyl chloride is carried out according to the known methods of the prior art.

Step (4) is carried out by adding an inorganic nitrate salt which cation is selected from metals belonging to the Groups IB and IIB, to a solution of the compound of formula (III), wherein X is halogen as above defined, or O-tosyl or O-mesyl, in an organic solvent wherein said nitrate salt should be soluble, such as for example acetonitrile, tetrahydrofuran. The cation of the salt can be zinc, silver or mercury. Preferably the salt is silver nitrate. The reaction temperature can range between 20° and 90° C. The synthesis appears to be specific:

when in the process object of the present invention are used as starting compounds other therapeutically active molecules having a reactive carboxylic function, it is found that the corresponding nitroxymethylphenyl esters are obtained with lower yields, as it is shown in the Examples.

The following Examples are given with the only purpose to illustrate the invention and they do not limit the same.

EXAMPLE 1

Preparation of the 2-(acetyloxy) benzoic acid 3-(nitroxymethyl)-phenyl ester

EXAMPLE 1a

Preparation of the 2-(acetyloxy)benzoic acid 3-(formyl)phenyl ester

A mixture of 3-hydroxybenzaldehyde (830 g) and triethylamine (8.24 g) in methylene chloride (12.6 l) is kept under stirring, in inert nitrogen atmosphere, cooling at a temperature between −5° C. and 0° C. Salicyloyl chloride (1650 g) is added in small portions in an hour. The mixture is still kept under stirring for 15 minutes, then water (10 l) is added and the phases are separated. The aqueous phase is recovered and apart extracted with methylene chloride (3 l). The organic phases are joined together, washed with a 5% $Na_2CO_3$ solution (5 l×2 times) and then with water (5 l×2 times). The organic phase is dried with magnesium sulphate (2 Kg) in the presence of decolorating carbon (300 g). It is filtered under vacuum and the solvent is evaporated at reduced pressure at a bath temperature lower than 40° C., at last obtaining 1929 g of 3-(formyl)phenyl ester of the 2-(acetoxy) benzoic acid (quantitative yield) m.p. 80–84° C. The compound purity determined by HPLC, by using a LiChrospher® 100 RP 8 column, eluent buffer phosphate pH 8/acetonitrile 55/45, was equal to 98.5%.

EXAMPLE 1b

Preparation of the 2-(acetyloxy)benzoic acid 3-(hydroxymethyl)phenyl ester

The 2-(acetyloxy)benzoic acid 3-(formyl)phenyl ester (1929 g) is dissolved in ethyl acetate (11 l) in the presence of 5% palladium on carbon (290 g) with the 50% of humidity.

The mixture is hydrogenated at room temperature and hydrogen pressure of about 2.5 atm, under stirring. The reaction during the first hour is slightly exothermic and the temperature in the reactor increases up to 35° C. After eight hours fresh catalyst (100 g) is added to complete the reaction. After 12 hours the reactor is discharged, the catalyst is removed by filtration under vacuum, in nitrogen atmosphere, washing the panel with ethyl acetate (2 l). The organic phases are joined together and are washed with a 5% sodium bicarbonate solution (3 l×2) and with water (3 l×2). The organic phase is dried with magnesium sulphate (2 Kg) in the presence of decolorating carbon (100 g). It is filtered under vacuum and evaporated at reduced pressure at a bath temperature lower than 40° C., obtaining 1,850 g of 2-(acetyloxy)benzoic acid 3-(hydroxymethyl)phenyl ester with yield of 95.2%, m.p. 77–79° C. The compound purity determined by HPLC, by using a LiChrospher® 100 RP 8 column, eluent buffer phosphate pH 8/acetonitrile 55/45, is equal to 99.0%.

EXAMPLE 1c

Preparation of the 2-(acetyloxy)benzoic acid 3-(chloromethyl) phenyl ester

To a mixture consituted by 2-(acetyloxy)benzoic acid 3-(hydroxymethyl)phenyl ester (1850 g) and thionyl chloride (5.5 l) kept under stirring, dimethylformamide (5 ml) is added at room temperature and is left under stirring for one hour. At last the thionyl chloride is evaporated at reduced pressure at a bath temperature lower than 40° C. The residual traces of thionyl chloride in the compound are eliminated treating the solid with toluene (2 l×2), which is then removed by evaporation at reduced pressure at a bath temperature lower than 40° C. The so obtained crude solid is purified by crystallization with isopropyl ether (30 l), removing by filtration the residue which remains undissolved in the crystallization solvent brought to the boiling temperature.

After cooling and filtration at reduced pressure, a solid is isolated which is dried under vacuum at room temperature, obtaining 1,367 g (yield 69.4%) of 2-(acetyloxy)benzoic acid 3-(chloromethyl) phenyl ester m.p. 71–73° C. The compound purity, determined by HPLC using a LiChrospher® 100 RP 8 column, eluent buffer phosphate pH 8/acetonitrile 40/60, is 99.0%.

EXAMPLE 1d

Preparation of the 2-(acetyloxy)benzoic acid 3-(nitroxymethyl) phenyl ester

A solution of 2-(acetyloxy)benzoic acid 3-(chloromethyl) phenyl ester (1,367 g) in acetonitrile (8 l) is treated under stirring, sheltered from the light and at room temperature with $AgNO_3$ (915 g). It is heated up to reflux for two hours and then it is cooled at room temperature and $AgNO_3$ (115 g) is added. It is heated again at reflux and after 4 hours it is cooled to 10° C.; the precipitate (silver salts) is filtered under vacuum and washed with acetonitrile (1 l×2). The organic phases are joined together and the solvent evaporated under vacuum at a bath temperature lower than 40° C. The residue is dissolved in chloroform (4 l), decolorating carbon (100 g) is added, it is stirred and the organic phase is percolated on a silica panel (2.5 Kg). The silica is washed with chloroform (10 l).

The organic phases are joined together and are concentrated to small volume at reduced pressure and bath temperature lower than 40° C. until in the solution the formation of a precipitate (about 3 l by volume) is noticed. The volume of the solution is maintained constant by continuously feeding isopropyl ether (6 l), continuing the chloroform evaporation at reduced pressure until its complete removal from the organic phase. The organic phase is left under stirring for two hours at the temperature of 20° C. It is filtered under vacuum washing with isopropyl ether (1.5 l) the solid on the filter. After drying under vacuum at room temperature, 1200 g of 2-(acetyloxy)benzoic acid 3-(nitroxymethyl) phenyl ester (yield 80.7%) m.p. 63.5–64° C., are isolated. The compound purity, determined by HPLC by using a LiChrospher® 100 RP 8 column, eluent buffer phosphate pH 8/acetonitrile 50/50, is 99.75%. The final product structure has been confirmed by $^1$H-NMR (CDCl$_3$): 8.22 (1H, dd), 7.66 (1H, td), 7.47 (1H, t), 7.40 (1H td), 7.32 (1H, d), 7.24–7.21 (2H, m), 7.18 (1H, dd), 5.44 (2H, s), 2.30 (3H, s).

The global process yield is 53.3%.

EXAMPLE 2

Preparation of the 2-(acetyloxy)benzoic acid 2-(nitroxymethyl phenyl ester

The product is prepared according to the procedure described in Example 1, by using as alcohol 2-hydroxybenzaldehyde. By analyzing the final compound obtained by chromatography on a thin layer of silica gel, using as eluent hexane/ethyl acetate 7/3, an unitary stain is obtained. The final product structure has been confirmed by $^1$H-NMR (CDCl$_3$): 8.22 (1H, dd), 7.68 (1H, dt), 7.35 (6H, m), 5.40 (2H, s), 2.30 (3H, s). The global process yield is 67.8%.

EXAMPLE 3

Preparation of the 2-(acetyloxy)benzoic acid 4-(nitroxymethyl)phenyl ester

The product is prepared according to the procedure described in Example 1. The used aromatic hydroxy-aldehyde is 4-hydroxybenzaldehyde. By thin layer of silica gel, using as eluent hexane/ethyl acetate 7/3, an unitay stain is obtained. The final product structure has been confirmed by $^1$H-NMR (CDCl$_3$): 8.21 (1H, dd), 7.66 (1H, dt), 7.42 (6H, m), 5.40 (2H, s), 2.25 (3H, s). The global process yield is 57.5%.

EXAMPLE 4

Preparation of the 1-(4-chlorobenzoyl)-5-methoxy-2-methyl-1H-indol-3-acetic acid 3-(nitroxymethyl) phenyl ester The product is prepared according to the procedure described in Example 1. The aromatic hydroxy-aldehyde used in step (1) is 3-hydroxybenzaldehyde. The global process yield is 39.1%. By analyzing the final product by chromatography on thin layer of silica gel, an unitary stain is obtained. M.p. 115–117° C. $^1$H-NMR (CDCl$_3$): 7.70 (2H, d), 7.49 (2H, d), 7.42 (1H, t), 7.14–7.06 (4H, m), 6.90 (1H, d), 6.70 (1H, dd), 5.42 (2H, s), 3.93 (2H, s), 3.86 (3H, s) 2.48 (3H, s).

What is claimed is:

1. A process for obtaining (nitroxymethyl)phenyl esters of aspirin derivatives of formula R—COOH wherein R is selected from one of the radicals having the following formula:

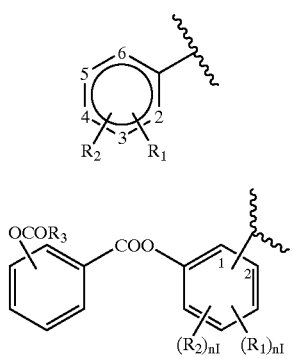

wherein:
- $R_1$ is the $OCOR_3$ group; wherein $R_3$ is methyl, ethyl or alkyl $C_3-C_5$ linear or branched, or the residue of a saturated heterocyclic ring having 5 or 6 atoms, containing hetero-atoms independently selected between O and N;
- $R_2$ is hydrogen, halogen, $C_1-C_4$ alkyl, linear or branched when possible, $C_1-C_4$ alkoxyl, linear or branched when possible; $C_1-C_4$ perfluoroalkyl, linear or branched when possible; nitro, mono- or di-$(C_{1-4})$ alkylamino;
- $R_1$ and $R_2$ taken together are the dioxymethylene group, with the proviso that in the formula Ib) $R_1$ cannot be $OCOR_3$ in position 2 when $R_3$ is methyl;
- nI is an integer and can take the values 0 or 1;

said synthesis process comprising the following steps:
(1) reaction between the halide R—C(O)—XI (A) wherein:

$X_I$ is Cl, Br, R being a radical as above defined, with an isomer of the hydroxy-benzaldehyde, in the presence of a base, with formation of a (carbonyl)phenyl ester;

(2) reduction of aldehydic group of the (carbonyl) phenyl ester with formation of an (hydroxymethyl)phenyl ester;

(3) reaction between (hydroxymethyl) phenyl ester of formula (II) with:
  a) $SoX_2$, X being an halogen selected between Cl and Br, or
  b) tosyl chloride or mesyl chloride (4) reaction between the ester isolated at the previous step with an inorganic nitrate salt, which metal cation belongs to the group IB or IIB, with formation of the (nitroxymethyl) phenyl ester.

2. A process according to claim 1, wherein the formation of the (carbonyl)phenyl ester expected in step (1) is alternatively carried out by reacting the aspirin derivative of formula R—COOH with a dehydrating agent in the presence of an aminopyridine derivative N, N di-substituted with alkyl radicals $C_1-C_4$, or of a $C_1-C_4$ alkylchloroformate in the presence of a base, or with N, N' carbonyldiimidazole.

3. A process according to claim 1, wherein the nitrate used in step (4) is silver nitrate.

4. A process according to claim 1, wherein the aspirin derivative of formula R—COOH is the acetylsalicylic acid.

5. (Hydroxymethyl)phenylester of aspirin derivatives of formula R—COOH, wherein R is as above defined in claim 1.

* * * * *